(12) United States Patent  
Brathwaite

(10) Patent No.: US 9,339,409 B2  
(45) Date of Patent: May 17, 2016

(54) WOMEN'S PORTABLE URINAL

(71) Applicant: Angela Brathwaite, Long Beach, CA (US)

(72) Inventor: Angela Brathwaite, Long Beach, CA (US)

(73) Assignee: Angela Brathwaite, Long Beach, CA (US)

( * ) Notice: Subject to any disclaimer, the term of this patent is extended or adjusted under 35 U.S.C. 154(b) by 189 days.

(21) Appl. No.: 14/120,313

(22) Filed: May 15, 2014

(65) Prior Publication Data

US 2015/0328041 A1 Nov. 19, 2015

(51) Int. Cl.
*A47K 11/00* (2006.01)
*A61F 5/455* (2006.01)

(52) U.S. Cl.
CPC .................................. *A61F 5/4556* (2013.01)

(58) Field of Classification Search
CPC ..................................................... A61F 5/4556
USPC .................................................. 4/144.1–144.3
See application file for complete search history.

(56) References Cited

U.S. PATENT DOCUMENTS

| | | | | |
|---|---|---|---|---|
| 3,643,266 A * | 2/1972 | Black | ................... | A47K 11/026 4/144.2 |
| 6,142,101 A * | 11/2000 | Pelsor | ................... | A01K 7/005 119/61.54 |
| 7,363,661 B1 * | 4/2008 | Myers | ................... | A47K 11/12 4/144.1 |
| D727,482 S * | 4/2015 | Brathwaite | ................... | 4/114.1 |
| 2008/0028503 A1 * | 2/2008 | Brown | ................... | A47K 11/12 4/144.1 |

* cited by examiner

*Primary Examiner* — Kristen Matter

(57) ABSTRACT

The Women's Portable Urinal is a molded plastic or metal piece that allows a person to relieve themselves in an emergency situation. It is designed to hold the liquid and allow any spillage while being stored and allows a very quick and easy emptying process. A top lid cover seals the unit so that no liquid can ever be spilled and becomes a very sanitary unit for its purpose.

1 Claim, 5 Drawing Sheets

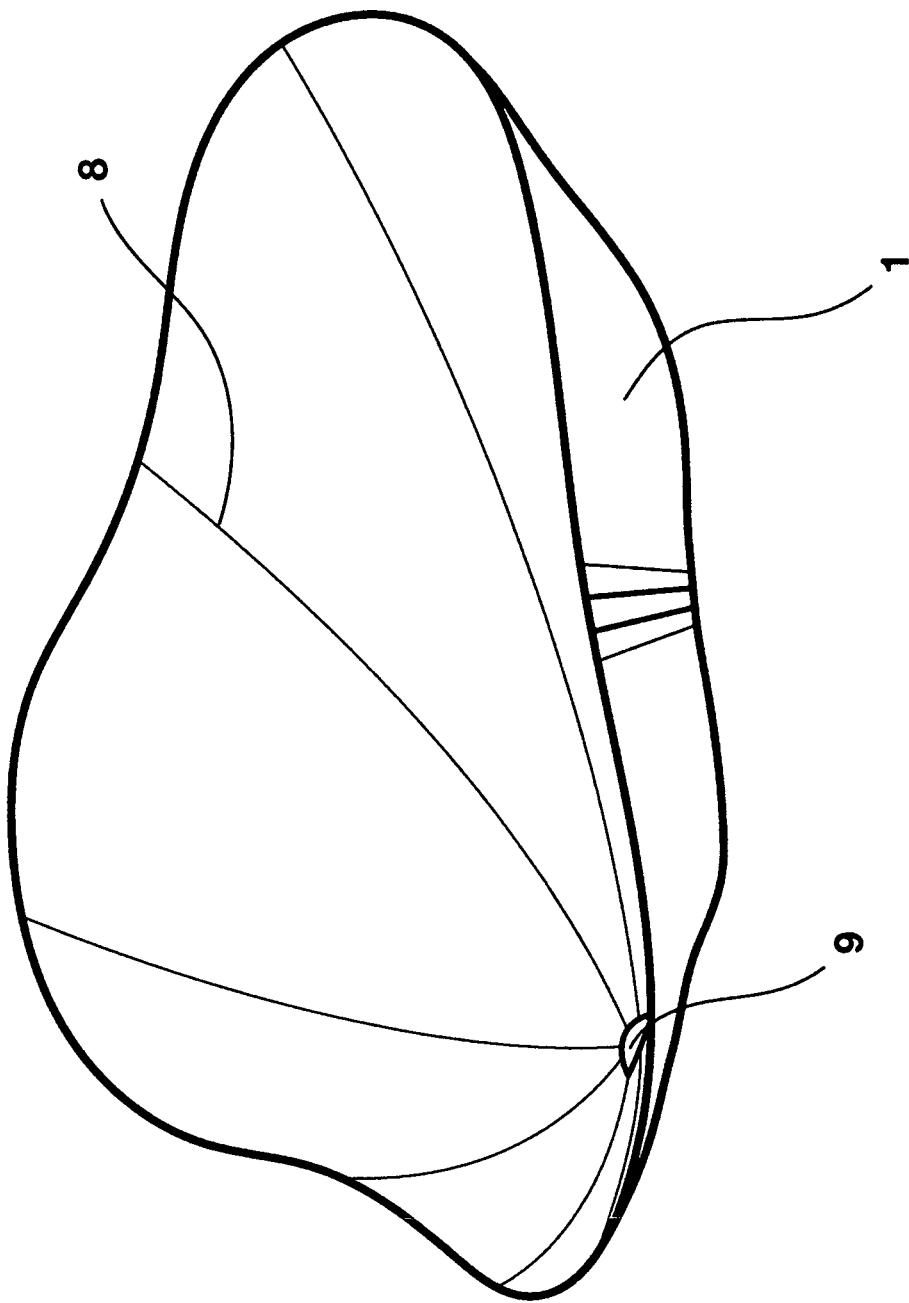

WOMEN'S PORTABLE URINAL

Figure 1:
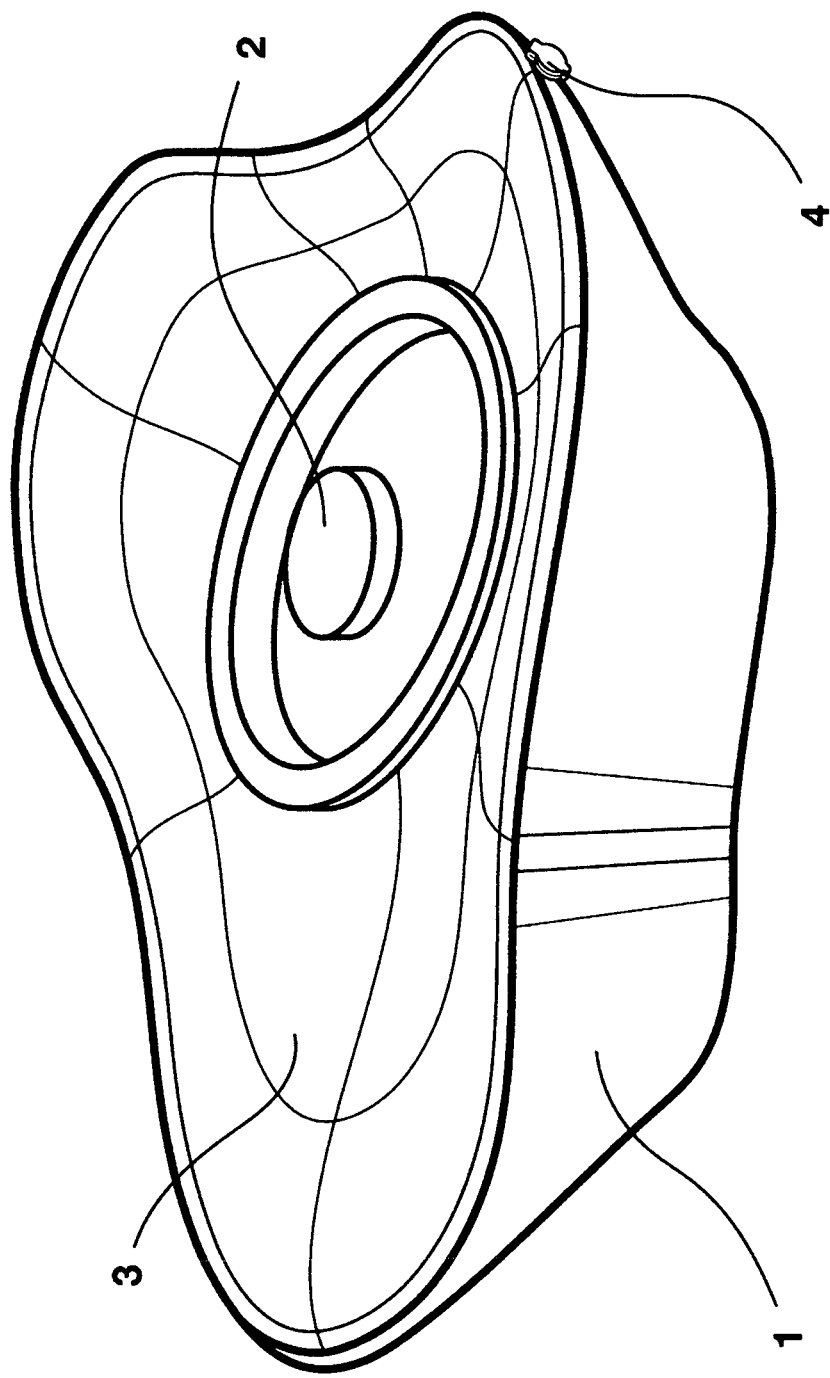

There is no federally sponsored or research or development associated with this application.

There is no joint research agreement associated with this application.

BACKGROUND OF THE INVENTION (1) Field of the Invention

The Women's Portable Urinal is unique to other portable urinals or bed pans.

(2) Description of the Art Including Information Disclosed Under 37 CFR 1.97 & 1.98

The art described in the drawings of the design and utility function illustrate the unique ability of the Women's Portable Urinal to be easy to use and is sanitary at the same time. U.S. Pat. No. 7,363,661 B1/Myers is of a similar nature to this application but it has a different design and different functionality. We found it to be not similar enough to pose a problem with this application

BRIEF SUMMARY OF THE INVENTION

The Women's Portable Urinal is a molded plastic design that allows a person to have a portable urinal for taking long trips or for an emergency situation where no restroom is available and the person is not in a good spot to relieve themselves. It can hold about 2 to 3 uses and will not spill any liquid and empties very quickly and easily. It maintains a sanitary condition at all times.

BRIEF DESCRIPTION OF THE SEVERAL VIEWS OF TILE DRAWINGS

There are 5 drawings in total that describe and illustrate the design and function of the Women's Portable Urinal. The lighter lines in the drawings are there to show the contour and radius of the curvatures of the invention.

FIG. 1: is the ¾ perspective showing the top, front, and side view.

Figure 2:
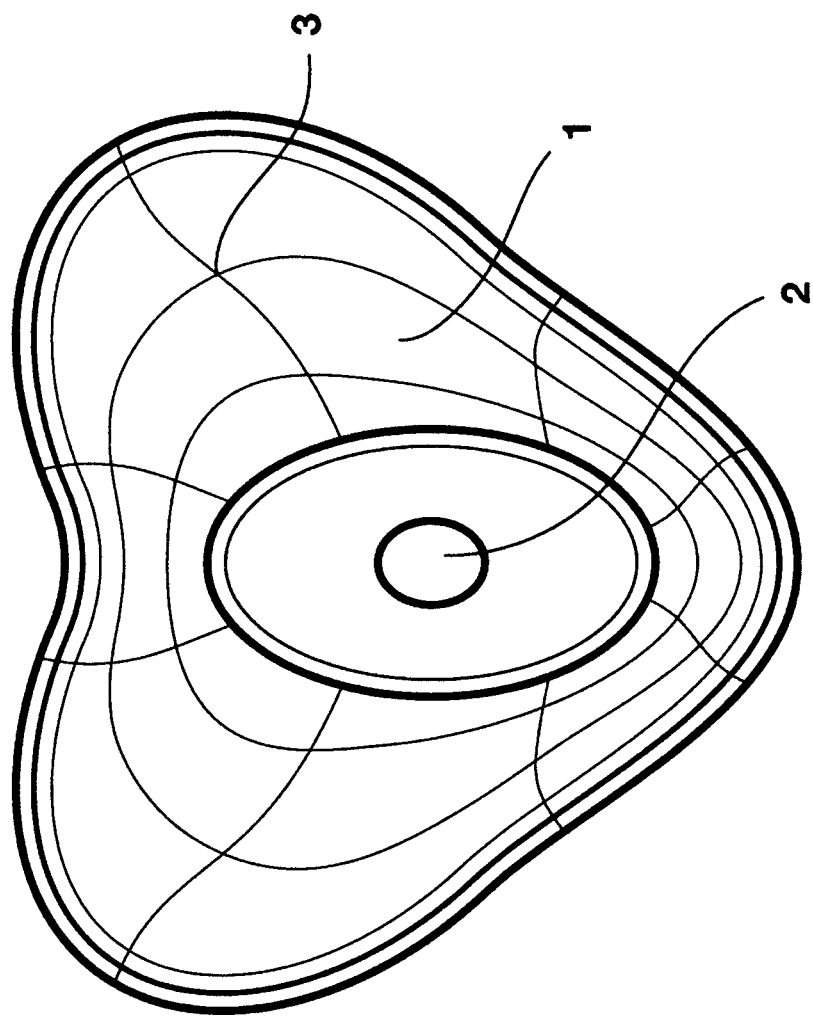
Figure 3:
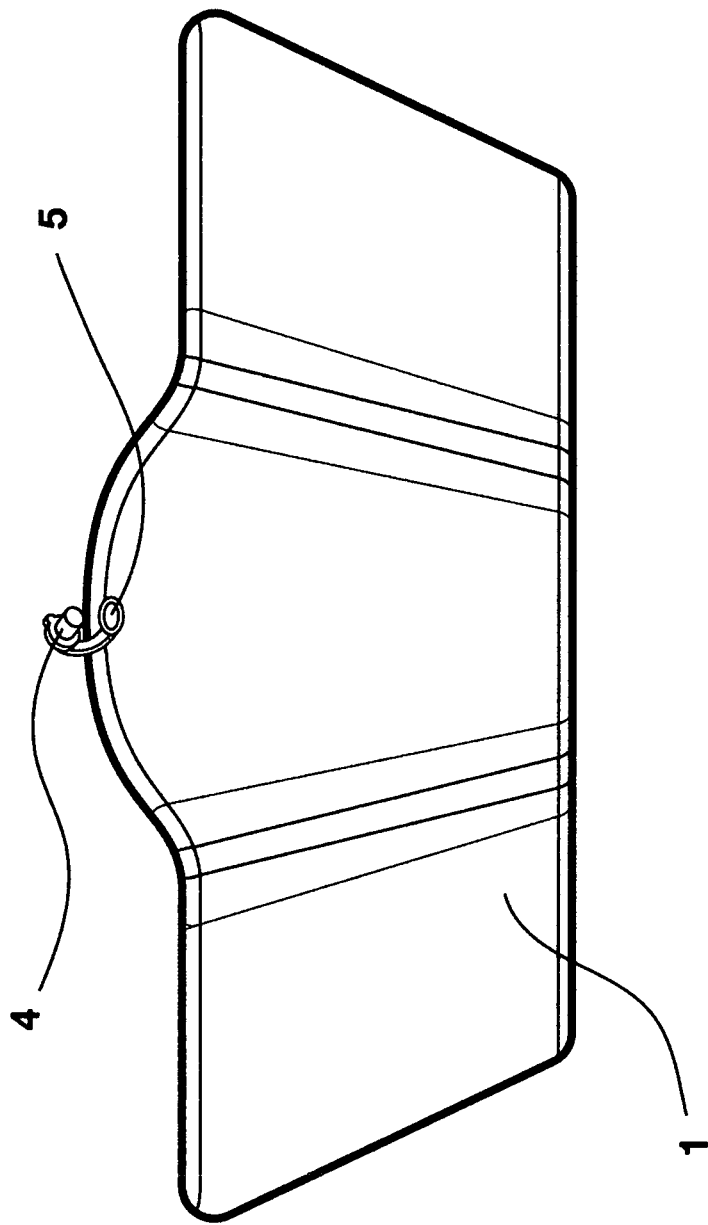
Figure 4:
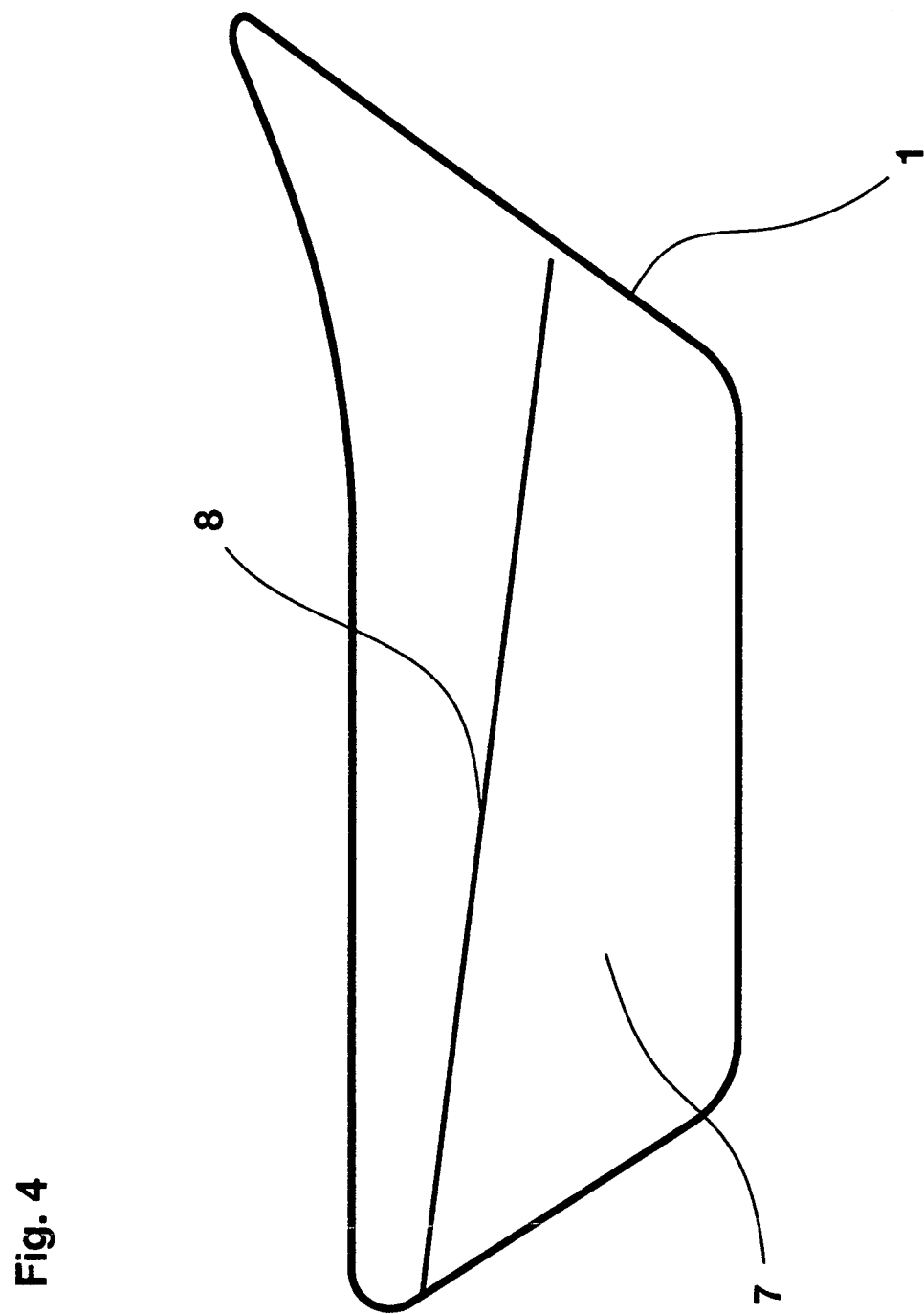

FIG. 2: is the top view.
FIG. 3: is the front view.
FIG. 4: is the side view.
FIG. 5: is the internal view.

DETAILED DESCRIPTION OF THE PREFERRED EMBODIMENT

FIG. 1: In this illustration #1 shows the main body portion of the invention that houses the molded center horizontal wall for the liquid to flow to the bottom of the main body portion with #2 the sealed lid cover that keeps any liquid from flowing out of the main body portion with #3 the contoured seat for the person's buttocks to form a seal when urinating with #4 the front top plug that is pulled out to allow the liquid to flow from the bottom portion and out of the #5 hole of the main body portion.

FIG. 2: In this illustration #1 shows the main body portion of the invention that houses the molded center horizontal wall for the liquid to flow to the bottom of the main body portion with #2 the sealed lid cover that keeps any liquid from flowing out of the main body portion with #3 the contoured seat for the person's buttocks to form a seal when urinating.

FIG. 3: In this illustration #1 shows the main body portion of the invention that houses the molded center horizontal wall for the liquid to flow to the bottom of the main body portion with #4 the front top plug that is pulled out to allow the liquid to flow from the bottom portion and out of the #5 hole of the main body portion.

FIG. 4: In this illustration #1 shows the main body portion of the invention that houses the molded center wall for the liquid to flow to the bottom of the main body portion with #7 the bottom portion of the main body portion that holds the liquid with #8 the center molded horizontal wall that is contoured and slanted to allow the flow of the liquid to the front center hole of the horizontal wall and to allow the urinal to be emptied from the bottom hole to the top front hole.

FIG. 5: In this illustration #1 shows the main body portion of the invention that houses the #8 molded center horizontal wall for the liquid to flow to the bottom of the main body portion with #9 the hole area that connects the horizontal center wall to the front of the main body portion so the liquid can flow into the bottom portion and to allow the liquid to flow upward to the front top hole for easy emptying of the urinal.

DETAILED DESCRIPTION OF THE INVENTION

The Women's Portable Urinal is a plastic molded design that is unique in the way it is designed and in the way it functions. It has a top piece that is contoured for person's buttocks to fit into the contour and form a seal for urinating into the large oval shaped hole in the center of the seat portion. It also has a lid cover that seals the large hole so that no liquid can leak from the main body of the invention. In the center of the main body of the portable urinal there is a molded horizontal wall or surface that is contoured and slanted to allow the liquid coming from the top seat portion to flow downward to the front of the main body to a hole located in the front center of the horizontal wall or surface and allow the liquid to flow to the bottom portion of the urinal. This makes the spilling of any liquid very unlikely and with the top lid cover it will keep any liquid inside of the main body without the chance to spill. When it is time to empty the urinal you simply angle the main body to the front and turn the unit upside down to the front top hole and the liquid will come out of that hole quickly and easily.

What is claimed is:

1. A portable urinal made of molded plastic or metal, said urinal comprising:
    a main body portion that is heart shaped;
    a top seat portion that is heart shaped and contoured for fitting the buttocks of a person;
    a large opening in the top seat portion, the large opening having an oval shape;
    a lid cover that seals the large opening;
    an opening or hole in a top front center of the main body portion;
    a removable plug for plugging the opening or hole in the top front center of the main body portion;
    a molded wall located in a center of the main body portion, the wall being contoured and angled downward towards a front of the main body portion; and
    an opening or hole in a front center portion of the wall, the opening or hole in the front center portion of the wall allowing liquid to flow into a bottom portion of the main body portion;
    wherein the urinal is configured such that all of the liquid can be emptied from the main body portion through the opening or hole in the top front center of the main body portion.

* * * * *